United States Patent
Bähnisch

(10) Patent No.: US 6,686,398 B1
(45) Date of Patent: Feb. 3, 2004

(54) METHOD AND ARRANGEMENT FOR PRODUCING METHANOL

(75) Inventor: Hans-Joachim Bähnisch, Dortmund (DE)

(73) Assignee: Uhde GmbH, Dortmund (DE)

(*) Notice: Subject to any disclaimer, the term of this patent is extended or adjusted under 35 U.S.C. 154(b) by 7 days.

(21) Appl. No.: 10/070,407

(22) PCT Filed: Aug. 31, 2000

(86) PCT No.: PCT/EP00/08486

§ 371 (c)(1), (2), (4) Date: Mar. 6, 2002

(87) PCT Pub. No.: WO01/17936

PCT Pub. Date: Mar. 15, 2001

(30) Foreign Application Priority Data

Sep. 7, 1999 (DE) .......... 199 42 736
Oct. 8, 1999 (DE) .......... 199 48 585

(51) Int. Cl.$^7$ .................... C07C 27/00
(52) U.S. Cl. .................... 518/706; 518/700
(58) Field of Search .................... 518/700, 706; 422/146, 235

(56) References Cited

U.S. PATENT DOCUMENTS 2,904,575 A 9/1959 Peet
5,179,129 A * 1/1993 Studer .......... 518/700

FOREIGN PATENT DOCUMENTS

| DE | 21 17 060 | 10/1972 |
|----|-----------|---------|
| DE | 25 29 591 | 1/1976 |
| DE | 32 20 995 | 12/1983 |
| DE | 35 18 362 | 11/1986 |
| DE | 41 00 632 | 4/1992 |
| DE | 40 04 862 | 1/1993 |
| DE | 40 28 750 | 6/1993 |
| WO | WO 97/31707 | 9/1997 |

* cited by examiner

Primary Examiner—J. Parsa
(74) Attorney, Agent, or Firm—Collard & Roe, P.C.

(57) ABSTRACT

By a method for the methanol synthesis from hydrogen, carbon monoxide and carbon dioxide under pressure, comprising at least one methanol reactor filled with catalyst, whereby in the presence of a plurality of stages, at least one stage is equipped with a compressor, and with a system for carrying out the method, the aim is to overcome the specified drawbacks, and in particular to make it possible to save heat exchanger surface area and/or to increase the yield, while particularly taking into account the changing activity of the catalyst. This is achieved according to the method in that in at least one synthesis stage, the gas mixture intended for us in a methanol reactor filled with catalyst is heated in an additional trimmer heater immediately before it added to said methanol reactor, whereby a corresponding system is characterized in that in at least one synthesis stage, provision is made for a trimmer heater (5) for heating the gas mixture directly impinging upon the methanol reactor (10). The single figure is to be published with the above.

4 Claims, 1 Drawing Sheet

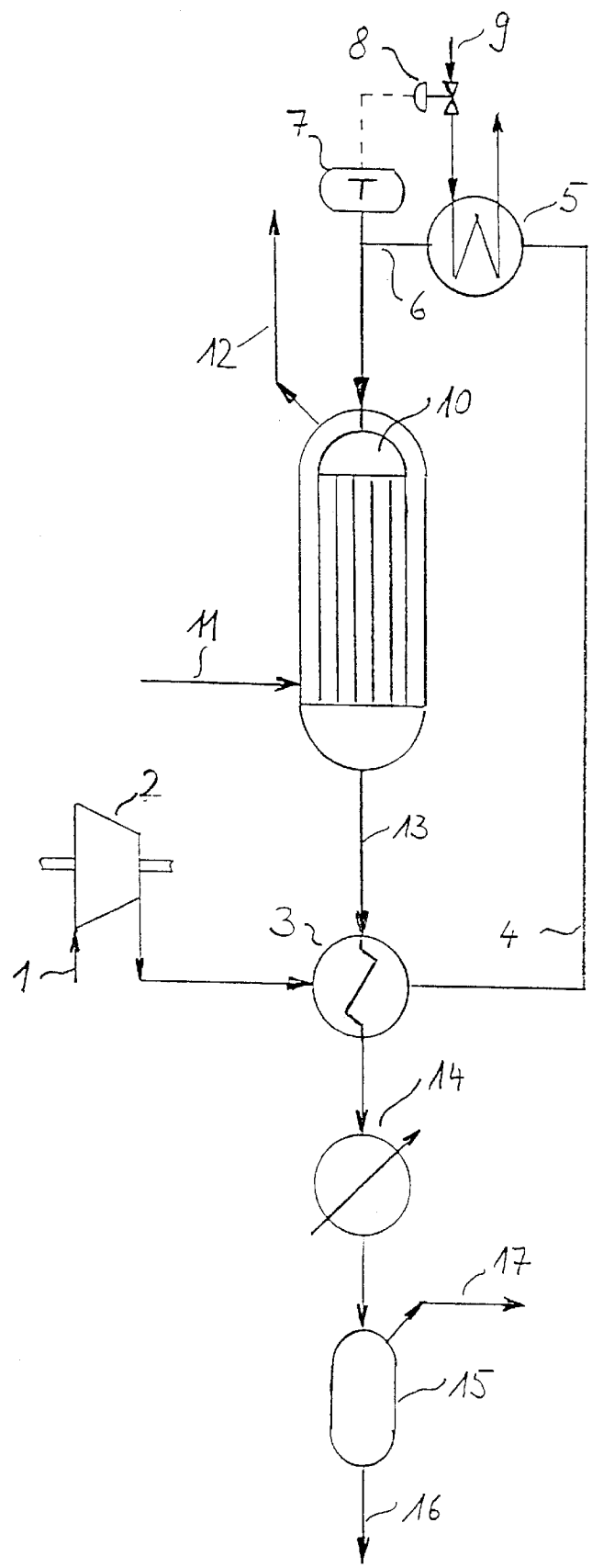

METHOD AND ARRANGEMENT FOR PRODUCING METHANOL

CROSS REFERENCE TO RELATED APPLICATIONS

Applicant claims priority under 35 U.S.C. §119 of German Application Nos. 199 42 736.4 and 199 48 585.2 filed Sep. 7, 1999 and Oct. 8, 1999, respectively. Applicant also claims priority under 35 U.S.C. §120 of PCT/EP00/08486 filed Aug. 31, 2000. The international application under PCT article 21(2) was not published in English.

The invention relates to a method for the methanol synthesis from hydrogen, carbon monoxide and carbon dioxide under pressure, comprising at least one synthesis stage of the type specified in the introductory part of claim 1; as well as to a system for such a synthesis.

A number of systems and methods for catalytic methanol syntheses are known. In light of the abundance of available solutions, the patent documents DE 21 17 060; DE 25 29 591; DE 32 20 995; DE 35 18 362; U.S. Pat. No. 2,904,575; and DE 41 00 632 are cited here as representative of such solutions.

A process is known from WO 97/31707 in which a trimmer heater is arranged upstream of a cooperating gas/gas heat exchanger, which reduces the temperature difference of the heat exchanger and thus increases its surface area. The aim of the present invention is to avoid such an increase of the surface area. WO 97/31707, furthermore, also describes a technology in connection with which the heat exchanger is integrated in the reactor. This necessarily leads to the necessity for having an additional heat exchanger because the conditions of the reaction are otherwise unstable.

In DE 40 28 750 of the present applicant firm, a furnace (=6 in said patent document) is employed for reaching the required reaction temperature on the inlet of the adiabatic reactor. Said furnace also serves as an indirect heater for a re-boiler (=11 in said patent document) employed in the distillation stage. Only a small portion of the reaction heat of the reactor is used there for heating the reaction inlet gases. The re-boiler only serves there the purpose of propelling the subsequent distillation.

DE 40 04 862 of the present applicant firm describes an additional heat exchanger which, however, is employed there only as a heat exchanger in the start-up phase. The use of said heat exchanger, however, does not result in any reduction of the remaining heat exchanger surface areas.

It is stated in DE 41 00 632 that it is advantageous to operate a number of synthesis stages with reactors, to condense the methanol produced by said reactors, to separate the methanol from the synthesis gas, and to extract the methanol downstream of each individual reactor in the form of a separate methanol product stream. In the cooling stage for cooling the methanol synthesis gas mixture exiting from the reactors, it is economical to use the heat to be dissipated at least partly for the purpose of preheating the inlet streams admitted into the individual reactors by means of gas/gas heat exchangers.

However, in the course of many years of operation it has been found to be a drawback that catalyst material normally used in the methanol reactors is subject to changes occurring in the course of time with respect to its activity in such a way that increasingly higher reactor temperatures are required in order to obtain an optimal yield, whereby, however, such higher reactor temperatures can no longer be reached after some time in the zones downstream of the gas inlet areas. Because of the reduced reaction turnover, both less methanol and also less steam are produced, which is normally collected in the cooling phase of the methanol reactors in the form of a coupled product.

The problem of the invention is to overcome the aforementioned drawbacks and in particular to provide the possibility for saving heat exchanger surface area and/or to increase the yield while particularly taking into account the change occurring in the catalyst activity.

In a process of the type specified above, said problem according to the invention is solved with the help of the characterizing features of claim 1. Provision is made in this connection that in at least one synthesis stage, the gas mixture intended for use in a methanol reactor filled with catalyst is directly heated in an additional trimmer heater before it is added to said methanol reactor.

Further developments of the invention comprise the following features, among other things:

The temperature of the gas mixture intended for use in the catalyst-filled reactors is measured after it has been heated by the additional trimmer heater;

the feed of heat into the additional trimmer heater can be controlled; and the additional trimmer heater is heated with a foreign medium, for example steam.

The principal advantage of such a procedure lies in that the gas/gas heat exchanger cooling the stream exiting from the reactor against the incoming stream can be designed with distinctly smaller dimensions. Furthermore, it was surprisingly found that with diminishing catalyst activity it is always possible to obtain an optimal yield by after-controlling the reactor inlet temperature.

Since the heat transfer properties of a, for example steam-heated trimmer heater are by multiple times superior to those of a gas/gas heat exchanger, and because the required safety reserve can be solely attributed to the trimmer heater, the result "under the bottom line" even includes savings of investment costs. Furthermore, it was found that the amount of steam used over the useful life of the catalyst is smaller than the loss of coupling product in case of loss due to reduced reaction turnover. The amount of steam generated thus increases "under the bottom line" in spite of the additional steam requirement. Furthermore, it was found that the start-up period of such a production plant can be substantially reduced if trimmer heaters can be used as starter heaters.

The problem stated above is solved with a system of the type specified above in that provision is made in at least one synthesis stage for a trimmer heater for heating the gas mixture that is directly acting on the methanol reactor.

Further developments of the system are specified in the system claims, whereby the advantages that have to be associated with said systems correspond with the advantages offered by the corresponding method.

BRIEF DESCRIPTION OF DRAWINGS

Additional advantages, details and features of the invention are disclosed in the following description as well as in the drawing. The drawing shows by a simplified representation a methanol synthesis system that is normally comprised of a number of stages that have identical structures, as a rule.

For compressing the feed gas denoted by 1, provision is made for a compressor 2, whereby provision is made in the downstream path of the flow of gas for a gas/gas heat exchanger 3 for preheating the feed gas. Via the line 4, the gas so preheated is supplied to a trimmer heater that heats the feed gas 1 to the desired temperature. For measuring the temperature, provision is made in the gas feed line 6 for a temperature measuring and controlling device 7, whereby the steam feed 9 is controlled by means of a steam control valve 8 in such a way that it is always possible to adjust an optimal gas inlet temperature in the methanol reactor 10 filled with catalyst.

The feed gas reacts in the catalyst-filled methanol reactor 10 under the development of heat. The reaction heat is used for generating the steam 12 for the feed water 11. The hot product gas 13 gives off a portion of its thermal energy in the gas/gas heat exchanger 3. The gaseous material produced in the reactor is condensed from the synthesis gas in the methanol condenser 14, separated from the synthesis gas in the condensate separator 15, and discharged as the product methanol 16. The remaining synthesis gas 17 can be used downstream in the subsequent stages.

In the system as defined by the invention, the reaction in the methanol reactor 10 is controlled mainly via a pressure control—not shown in the figure in detail—for the cooling medium (water 11, or steam 12), which surrounds the catalyst-filled tubes. If the activity of the catalyst diminishes, the entire temperature level has to be raised, which is carried out by increasing the pressure of the cooling medium, causing the evaporation temperature of the cooling medium to rise. This raises the temperature in the reactor and the exit temperature 13 rises as well.

The temperature in the line 4 rises via the heat exchanger 3 as well; however, not to the extent required for reaching optimal reaction conditions. This rise is accomplished with the help of the trimmer heater. It is therefore obvious that the basic function of the trimmer heater is to reduce the surface area requirements of the gas/gas heat exchanger 3, which is achieved on the one hand by increasing the temperature difference, and on the other hand by making it possible to omit the usual safety addition of surface area. This is particularly accomplished on account of the fact that the heat transfer in the trimmer heater is superior by a factor seven. The addition of surface area is therefore much smaller in the trimmer heater than in the heat exchanger, which constitutes an important advantage of the present invention.

The exemplified embodiment of the invention naturally still can be modified in many respects without vacating the basic idea of the invention. For example, the trimmer heater may comprise two stages, if need be, and the like, apart from many other modifications.

What is claimed is:

1. A method for the synthesis of methanol from hydrogen, carbon monoxide and carbon dioxide under pressure, comprising at least one synthesis stage containing at least one methanol reactor filled with a catalyst, whereby in the presence of a plurality of stages, at least one stage is equipped with a compressor, and whereby all synthesis stages are equipped with their own product extraction systems for withdrawing methanol and their own gas/gas heat exchangers for transferring thermal energy of a gas mixture exiting from the methanol reactor, to a gas mixture intended for use in the methanol reactor; and in at least one synthesis stage, heating the gas mixture intended for use in a catalyst-filled methanol reactor in an additional trimmer heater immediately before it is added to said methanol reactor.

2. The method according to claim 1, comprising measuring the temperature of the gas mixture intended for use in a methanol reactor filled with catalyst after it has been heated by the trimmer heater.

3. The method according to claim 1, comprising controlling the heat feed of the trimmer heater.

4. The method according to claim 1, comprising heating the trimmer heater with a foreign medium comprising steam.

* * * * *